US009896500B2

(12) United States Patent
Yugawa et al.

(10) Patent No.: US 9,896,500 B2
(45) Date of Patent: Feb. 20, 2018

(54) ANTIBODY CAPABLE OF BINDING TO INFLUENZA VIRUS

(71) Applicant: Panasonic Intellectual Property Management Co., Ltd., Osaka (JP)

(72) Inventors: Keiko Yugawa, Nara (JP); Jin Muraoka, Kyoto (JP); Junko Muraoka, Kyoto (JP); Hiroshi Nakayama, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 15/388,196

(22) Filed: Dec. 22, 2016

(65) Prior Publication Data
US 2017/0283485 A1  Oct. 5, 2017

Related U.S. Application Data

(60) Provisional application No. 62/316,672, filed on Apr. 1, 2016.

(51) Int. Cl.
*C07K 16/10* (2006.01)
(52) U.S. Cl.
CPC ...... *C07K 16/1018* (2013.01); *C07K 2317/22* (2013.01); *C07K 2317/569* (2013.01)
(58) Field of Classification Search
None
See application file for complete search history.

(56) References Cited

U.S. PATENT DOCUMENTS

2010/0330080 A1* 12/2010 Dreier ............... C07K 16/2866
424/133.1
2014/0302063 A1  10/2014 Hufton

FOREIGN PATENT DOCUMENTS

CN  103804493  5/2014

OTHER PUBLICATIONS

Simon E. Hufton et al., "The Breadth of Cross Sub-Type Neutralisation Activity of a Single Domain Antibody to Influenza Hemagglutinin Can Be Increased by Antibody Valency", PLOS ONE [www.plosone.org], Aug. 2014, vol. 9, Issue 8, e103294, pp. 1-19.

* cited by examiner

*Primary Examiner* — Nianxiang Zou
(74) *Attorney, Agent, or Firm* — McDermott Will & Emery LLP

(57) ABSTRACT

The present invention provides a novel antibody capable of binding influenza virus. The antibody directed to the present invention consists of an amino acid sequence, wherein said amino acid sequence consists of, in an N- to C-direction, the following structural domains:

N-FR1-CDR1-FR2-CDR2-FR3-CDR3-FR4-C

FR denotes a framework region amino acid sequence and CDR denotes a complementary determining region amino acid sequence;
the CDR1 consists of an amino acid sequence represented by SYYMS (SEQ ID NO: 01)
the CDR2 consists of an amino acid sequence represented by TINTGGGSTYYADSVKG (SEQ ID NO: 02);
the CDR3 consists of an amino acid sequence represented by DGPYGGYDY (SEQ ID NO: 03); and
the antibody is capable of binding to H12N1 influenza virus.

Desirably, the FR1-FR4 consist of amino acid sequences represented by EVQLVESGGGLVQPGGSLRVSCAASGFTFS (SEQ ID NO: 04), WVRQAPGKGLEWVS (SEQ ID NO: 05), RFTISRDNAKNTLYLQMDSLKSEDTAVYYCAK (SEQ ID NO: 06), and WGQGTQVTVSP (SEQ ID NO: 07), respectively.

2 Claims, 10 Drawing Sheets

SEQUENCE LISTING

```
<160> NUMBER OF SEQ ID NOS: 26

<210> SEQ ID NO 1
<211> LENGTH: 5
<212> TYPE: PRT
<213> ORGANISM: Lama pacos

<400> SEQUENCE: 1

Ser Tyr Tyr Met Ser
1               5
```

-continued

```
<210> SEQ ID NO 2
<211> LENGTH: 17
<212> TYPE: PRT
<213> ORGANISM: Lama pacos

<400> SEQUENCE: 2

Thr Ile Asn Thr Gly Gly Gly Ser Thr Tyr Tyr Ala Asp Ser Val Lys
1               5                   10                  15
Gly

<210> SEQ ID NO 3
<211> LENGTH: 9
<212> TYPE: PRT
<213> ORGANISM: Lama pacos

<400> SEQUENCE: 3

Asp Gly Pro Tyr Gly Gly Tyr Asp Tyr
1               5

<210> SEQ ID NO 4
<211> LENGTH: 30
<212> TYPE: PRT
<213> ORGANISM: Lama pacos

<400> SEQUENCE: 4

Glu Val Gln Leu Val Glu Ser Gly Gly Leu Val Gln Pro Gly Gly
1               5                   10                  15

Ser Leu Arg Val Ser Cys Ala Ala Ser Gly Phe Thr Phe Ser
                20                  25                  30

<210> SEQ ID NO 5
<211> LENGTH: 14
<212> TYPE: PRT
<213> ORGANISM: Lama pacos

<400> SEQUENCE: 5

Trp Val Arg Gln Ala Pro Gly Lys Gly Leu Glu Trp Val Ser
1               5                   10

<210> SEQ ID NO 6
<211> LENGTH: 32
<212> TYPE: PRT
<213> ORGANISM: Lama pacos

<400> SEQUENCE: 6

Arg Phe Thr Ile Ser Arg Asp Asn Ala Lys Asn Thr Leu Tyr Leu Gln
1               5                   10                  15

Met Asp Ser Leu Lys Ser Glu Asp Thr Ala Val Tyr Tyr Cys Ala Lys
                20                  25                  30

<210> SEQ ID NO 7
<211> LENGTH: 11
<212> TYPE: PRT
<213> ORGANISM: Lama pacos

<400> SEQUENCE: 7

Trp Gly Gln Gly Thr Gln Val Thr Val Ser Pro
1               5                   10

<210> SEQ ID NO 8
<211> LENGTH: 118
<212> TYPE: PRT
<213> ORGANISM: Lama pacos
```

<400> SEQUENCE: 8

Glu Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Asn Thr Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Ser Glu Asp Thr Ala Val Tyr Tyr Cys
                85                  90                  95

Ala Lys Asp Gly Pro Tyr Gly Gly Tyr Asp Tyr Trp Gly Gln Gly Thr
            100                 105                 110

Gln Val Thr Val Ser Pro
        115

<210> SEQ ID NO 9
<211> LENGTH: 15
<212> TYPE: DNA
<213> ORGANISM: Artificial Sequence
<220> FEATURE:
<223> OTHER INFORMATION: Synthesized Primer

<400> SEQUENCE: 9
ggtggtcctg gctgc                                                15

<210> SEQ ID NO 10
<211> LENGTH: 50
<212> TYPE: DNA
<213> ORGANISM: Artificial Sequence
<220> FEATURE:
<223> OTHER INFORMATION: Synthesized Primer

<400> SEQUENCE: 10
ctgctcctcg cggcccagcc ggccatggct sagktgcagc tcgtggagtc           50

<210> SEQ ID NO 11
<211> LENGTH: 21
<212> TYPE: DNA
<213> ORGANISM: Artificial Sequence
<220> FEATURE:
<223> OTHER INFORMATION: Synthesized Primer

<400> SEQUENCE: 11
tggggtcttc gctgtggtgc g                                         21

<210> SEQ ID NO 12
<211> LENGTH: 21
<212> TYPE: DNA
<213> ORGANISM: Artificial Sequence
<220> FEATURE:
<223> OTHER INFORMATION: Synthesized Primer

<400> SEQUENCE: 12
ttgtggtttt ggtgtcttgg g                                         21

<210> SEQ ID NO 13
<211> LENGTH: 45
<212> TYPE: DNA
<213> ORGANISM: Artificial Sequence

```
<220> FEATURE:
<223> OTHER INFORMATION: Synthesized Primer

<400> SEQUENCE: 13
tttgctctgc ggccgcagag gccgtggggt cttcgctgtg gtgcg                    45

<210> SEQ ID NO 14
<211> LENGTH: 46
<212> TYPE: DNA
<213> ORGANISM: Artificial Sequence
<220> FEATURE:
<223> OTHER INFORMATION: Synthesized Primer

<400> SEQUENCE: 14
tttgctctgc ggccgcagag gccgattgtg gttttggtgt cttggg                   46

<210> SEQ ID NO 15
<211> LENGTH: 13
<212> TYPE: DNA
<213> ORGANISM: Artificial Sequence
<220> FEATURE:
<223> OTHER INFORMATION: Synthesized DNA which represents SfiI(a) site

<400> SEQUENCE: 15
ggcccagccg gcc                                                       13

<210> SEQ ID NO 16
<211> LENGTH: 13
<212> TYPE: DNA
<213> ORGANISM: Artificial Sequence
<220> FEATURE:
<223> OTHER INFORMATION: Synthesized DNA which represents SfiI(b) site

<400> SEQUENCE: 16
ggcctctgcg gcc                                                       13

<210> SEQ ID NO 17
<211> LENGTH: 4057
<212> TYPE: DNA
<213> ORGANISM: Artificial Sequence
<220> FEATURE:
<223> OTHER INFORMATION: Synthesized plamid Vector 1

<400> SEQUENCE: 17
gacgaaaggg cctcgtgata cgcctatttt tataggttaa tgtcatgata ataatggttt    60
cttagacgtc aggtggcact tttcggggaa atgtgcgcgg aacccctatt tgtttatttt   120
tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gttttgctc acccagaaac gctggtgaaa gtaaaagatg    300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga caccacgatg cctgtagcaa tggcaacaac gttgcgcaaa ctattaactg   780
```

```
gcgaactact tactctagct tcccggcaac aattaataga ctggatggag gcggataaag      840
ttgcaggacc acttctgcgc tcggcccttc cggctggctg gtttattgct gataaatctg      900
gagccggtga gcgtgggtct cgcggtatca ttgcagcact ggggccagat ggtaagccct      960
cccgtatcgt agttatctac acgacgggga gtcaggcaac tatggatgaa cgaaatagac     1020
agatcgctga gataggtgcc tcactgatta agcattggta actgtcagac caagtttact     1080
catatatact ttagattgat ttaaaacttc attttaatt taaaaggatc taggtgaaga     1140
tcctttttga taatctcatg accaaaatcc cttaacgtga gttttcgttc cactgagcgt     1200
cagaccccgt agaaaagatc aaaggatctt cttgagatcc ttttttctg cgcgtaatct     1260 gctgcttgca acaaaaaaa ccaccgctac cagcggtggt ttgtttgccg gatcaagagc     1320
taccaactct ttttccgaag gtaactggct tcagcagagc gcagatacca atactgtcc     1380 ttctagtgta gccgtagtta ggccaccact tcaagaactc tgtagcaccg cctacatacc     1440
tcgctctgct aatcctgtta ccagtggctg ctgccagtgg cgataagtcg tgtcttaccg     1500
ggttggactc aagacgatag ttaccggata aggcgcagcg gtcgggctga acggggggtt     1560
cgtgcacaca gcccagcttg gagcgaacga cctacaccga actgagatac ctacagcgtg     1620
agctatgaga aagcgccacg cttcccgaag ggagaaaggc ggacaggtat ccggtaagcg     1680
gcagggtcgg aacaggagag cgcacgaggg agcttccagg gggaaacgcc tggtatcttt     1740
atagtcctgt cgggtttcgc cacctctgac ttgagcgtcg atttttgtga tgctcgtcag     1800
gggggcggag cctatggaaa aacgccagca acgcggcctt tttacggttc ctggccttt     1860 gctggccttt tgctcacatg ttctttcctg cgttatcccc tgattctgtg ataaccgta     1920 ttaccgcctt tgagtgagct gataccgctc gccgcagccg aacgaccgag cgcagcgagt     1980
cagtgagcga ggaagcggaa gagcgcccaa tacgcaaacc gcctctcccc gcgcgttggc     2040
cgattcatta atgcagctgg cacgacaggt ttcccgactg gaaagcgggc agtgagcgca     2100
acgcaattaa tgtgagttag ctcactcatt aggcaccca ggctttacac tttatgcttc     2160
cggctcgtat gttgtgtgga attgtgagcg ataacaatt tcacacagga aacagctatg     2220
accatgatta cgccaagctt cgaaggagac agtcataatg aaatacctgc tgccgaccgc     2280
tgctgctggt ctgctgctcc tcgcggccca gccggccatg gagctcaaga tgacacagac     2340
tacatcctcc ctgtcagcct ctctgggaga cagagtcacc atcagttgca gggcaagtca     2400
ggacattagc gattatttaa actggtatca gcagaaacca gatggaactg ttaaactcct     2460
gatctattac acatcaagtt tacactcagg agtcccatca aggttcagtg gcggtgggtc     2520
tggaacagat tattctctca ccattagcaa cctggagcaa aagatattg ccacttactt     2580 ttgccaacag ggtaatacgc ttccgtggac gtttggtgga ggcaccaagc tggaaatcaa     2640
acgggctgat gctgcaccaa ctgtaggcct ctgcggccgc agagcaaaaa ctcatctcag     2700
aagaggatct gaatgggggcc gcataggggt ccggtgattt tgattatgaa agatggcaa     2760 acgctaataa gggggctatg accgaaaatg ccgatgaaaa cgcgctacag tctgacgcta     2820
aaggcaaact tgattctgtc gctactgatt acggtgctgc tatcgatggt tcattggtg     2880 acgtttccgg ccttgctaat ggtaatggtg ctactgtga ttttgctggc tctaattccc     2940
aaatggctca agtcggtgac ggtgataatt cacctttaat gaataatttc cgtcaatatt     3000
taccttccct ccctcaatcg gttgaatgtc gcccttttgt ctttagcgct ggtaaaccat     3060 atgaatttc tattgattgt gacaaaataa acttattccg tggtgtcttt gcgtttcttt     3120
tatatgttgc cacctttatg tatgtatttt ctacgtttgc taacatactg cgtaataagg     3180
```

```
agtcttaata agaattcact ggccgtcgtt ttacaacgtc gtgactggga aaaccctggc    3240
gttacccaac ttaatcgcct tgcagcacat ccccctttcg ccagctggcg taatagcgaa    3300
gaggcccgca ccgatcgccc ttcccaacag ttgcgcagcc tgaatggcga atggcgcctg    3360
atgcggtatt ttctccttac gcatctgtgc ggtatttcac accgcatatg aaaattgtaa    3420
gcgttaatat tttgttaaaa ttcgcgttaa attttgtta aatcagctca ttttttaacc    3480
aataggccga atcggcaaa atcccttata aatcaaaaga atagaccgag ataggggtta    3540
gtgttgttcc agtttggaac aagagtccac tattaaagaa cgtggactcc aacgtcaaag    3600
ggcgaaaaac cgtctatcag ggcgatggcc cactacgtga accatcaccc taatcaagtt    3660
ttttggggtc gaggtgccgt aaagcactaa atcggaaccc taaagggagc ccccgattta    3720
gagcttgacg gggaaagccg gcgaacgtgg cgagaaagga agggaagaaa gcgaaaggag    3780
cgggcgctag ggcgctggca agtgtagcgg tcacgctgcg cgtaaccacc acccgccg    3840 cgcttaatgc gccgctacag ggcgcgtccc atatggtgca ctctcagtac aatctgctct    3900
gatgccgcat agttaagcca gccccgacac ccgccaacac ccgctgacgc gccctgacgg    3960
gcttgtctgc tcccggcatc cgcttacaga caagctgtga ccgtctccgg gagctgcatg    4020
tgtcagaggt tttcaccgtc atcaccgaaa cgcgcga                             4057

<210> SEQ ID NO 18
<211> LENGTH: 354
<212> TYPE: DNA
<213> ORGANISM: Artificial Sequence
<220> FEATURE:
<223> OTHER INFORMATION: Synthesized DNA coding for anti-H12N1 VHH
      antibody

<400> SEQUENCE: 18
gaggtgcagc tcgtggagtc tgggggaggc ttggtgcagc ctgggggtc tctgagagtc     60 tcctgtgcag cctctggatt caccttcagt agctactaca tgagctgggt ccgccaggct    120
ccagggaagg ggctcgagtg ggtctcaact attaatactg gtggtggtag cacatactat    180
gcagactccg tgaagggccg attcaccatc tccagagaca cgccaagaa cacccctctat   240 ctgcaaatgg acagtctgaa atctgaagat acagccgtgt attattgtgc aaaagatggg    300
ccatatggcg ggtacgacta ctggggccag gggacccagg tcaccgtctc ccca          354

<210> SEQ ID NO 19
<211> LENGTH: 30
<212> TYPE: DNA
<213> ORGANISM: Artificial Sequence
<220> FEATURE:
<223> OTHER INFORMATION: Synthesized Primer

<400> SEQUENCE: 19
gccggctggg ccgcgaggag cagcagacca                                      30

<210> SEQ ID NO 20
<211> LENGTH: 30
<212> TYPE: DNA
<213> ORGANISM: Artificial Sequence
<220> FEATURE:
<223> OTHER INFORMATION: Synthesized Primer

<400> SEQUENCE: 20
gcccagccgg ccatggccat ggatatcgga                                      30
```

```
<210> SEQ ID NO 21
<211> LENGTH: 96
<212> TYPE: DNA
<213> ORGANISM: Artificial Sequence
<220> FEATURE:
<223> OTHER INFORMATION: Synthesized Primer

<400> SEQUENCE: 21
catggatatc ggaattaatt cggatccgac tacaaagacc atgacggtga ttataaagat      60
catgacatcc tcgagcacca ccaccaccac cactga                               96

<210> SEQ ID NO 22
<211> LENGTH: 96
<212> TYPE: DNA
<213> ORGANISM: Artificial Sequence
<220> FEATURE:
<223> OTHER INFORMATION: Synthesized Primer

<400> SEQUENCE: 22
tcagtggtgg tggtggtggt gctcgaggat gtcatgatct ttataatcac cgtcatggtc      60
tttgtagtcg gatccgaatt aattccgata tccatg                               96

<210> SEQ ID NO 23
<211> LENGTH: 74
<212> TYPE: DNA
<213> ORGANISM: Artificial Sequence
<220> FEATURE:
<223> OTHER INFORMATION: Synthesized Primer

<400> SEQUENCE: 23
aaatacctgc tgccgccatg gatatcggaa ttaattcggc ctctgcggcc gcaggatccg      60
actacaaaga ccat                                                       74

<210> SEQ ID NO 24
<211> LENGTH: 74
<212> TYPE: DNA
<213> ORGANISM: Artificial Sequence
<220> FEATURE:
<223> OTHER INFORMATION: Synthesized Primer

<400> SEQUENCE: 24
atggtctttg tagtcggatc ctgcggccgc agaggccgaa ttaattccga tatccatggc      60
ggcagcaggt attt                                                       74

<210> SEQ ID NO 25
<211> LENGTH: 520
<212> TYPE: DNA
<213> ORGANISM: Artificial Sequence
<220> FEATURE:
<223> OTHER INFORMATION: Synthesized DNA including the gene sequence
      coding for the amino acid sequence represented by SEQ ID NO: 08

<400> SEQUENCE: 25
ggcccagccg gccatggctg aggtgcagct cgtggagtct gggggaggct tggtgcagcc      60 tgggggtct ctgagagtct cctgtgcagc ctctggattc accttcagta gctactacat      120
gagctgggtc cgccaggctc cagggaaggg gctcgagtgg gtctcaacta ttaatactgg      180
tggtggtagc acatactatg cagactccgt gaagggccga ttcaccatct ccagagacaa      240
cgccaagaac accctctatc tgcaaatgga cagtctgaaa tctgaagata cagccgtgta      300
ttattgtgca aaagatgggc catatggcgg gtacgctac tggggccagg ggacccaggt      360
caccgtctcc ccagcgcacc acagcgaaga ccccacggcc tctgcggccg caggatccga      420
```

-continued

```
ctacaaagac catgacggtg attataaaga tcatgacatc gattacaaag atgacgatga    480
caaactcgag caccaccacc accaccactg atctgcggcc                          520

<210> SEQ ID NO 26
<211> LENGTH: 507
<212> TYPE: DNA
<213> ORGANISM: Artificial Sequence
<220> FEATURE:
<223> OTHER INFORMATION: Synthesized DNA obtained by SfiI-treating the
      DNA represented by SEQ ID NO: 25

<400> SEQUENCE: 26
cggccatggc tgaggtgcag ctcgtggagt ctgggggagg cttggtgcag cctggggggt     60
ctctgagagt ctcctgtgca gcctctggat tcaccttcag tagctactac atgagctggg    120
tccgccaggc tccagggaag gggctcgagt gggtctcaac tattaatact ggtggtggta    180
gcacatacta tgcagactcc gtgaagggcc gattcaccat ctccagagac aacgccaaga    240
acaccctcta tctgcaaatg gacagtctga aatctgaaga tacagccgtg tattattgtg    300
caaaagatgg gccatatggc gggtacgact actggggcca ggggacccag gtcaccgtct    360
ccccagcgca ccacagcgaa gaccccacgg cctctgcggc cgcaggatcc gactacaaag    420
accatgacgg tgattataaa gatcatgaca tcgattacaa agatgacgat gacaaactcg    480
agcaccacca ccaccaccac tgatctg                                        507
```

ANTIBODY CAPABLE OF BINDING TO INFLUENZA VIRUS

INCORPORATION BY REFERENCE—SEQUENCE LISTING

The material contained in the ASCII text file named "P0625705_ST25.txt" created on Oct. 19, 2016 and having a file size of 13,716 bytes is incorporated by reference herein.

BACKGROUND

1. Technical Field

The present invention relates to an antibody capable of binding to an influenza virus.

2. Description of the Related Art

Patent Literature 1 discloses antibodies each capable of binding to an influenza virus. At least a part of the antibodies disclosed in Patent Literature 1 are derived from an alpaca. Patent Literature 1 is incorporated herein by reference.

CITATION LIST

Patent Literature

United States Patent Application Publication No. 2014/0302063

SUMMARY

An object of the present invention is to provide a novel antibody capable of binding to an influenza virus.

The present invention is an antibody that consists of an amino acid sequence, wherein said amino acid sequence consists of, in an N- to C-direction, the following structural domains:

N-FR1-CDR1-FR2-CDR2-FR3-CDR3-FR4-C wherein
  FR denotes a framework region amino acid sequence and CDR denotes a complementary determining region amino acid sequence;
  the CDR1 consists of an amino acid sequence represented by SYYMS (SEQ ID NO: 01);
  the CDR2 consists of an amino acid sequence represented by TINTGGGSTYYADSVKG (SEQ ID NO: 02);
  the CDR3 consists of an amino acid sequence represented by DGPYGGYDY (SEQ ID NO: 03); and
  the antibody is capable of binding to H12N1 influenza virus.

The present invention provides a novel antibody capable of binding to an influenza virus.

DETAILED DESCRIPTION OF THE EMBODIMENT

Figure 1A:
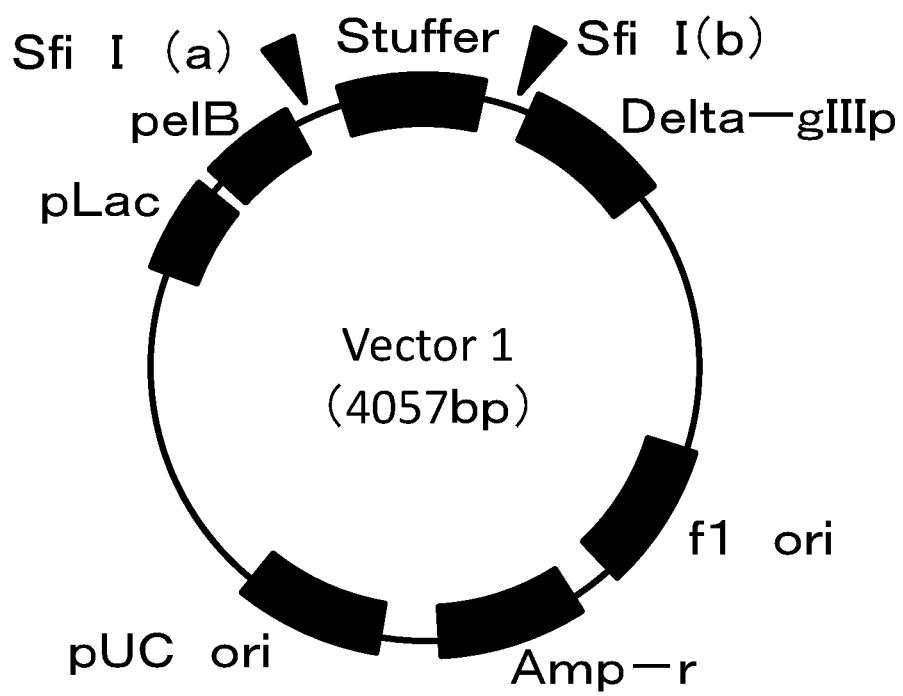
FIG. 1A is a map of a vector used to ligate various genes included in a gene library of a VHH antibody.

The antibody according to the present invention is capable of binding to an influenza virus H12N1. As disclosed in Patent Literature 1, an antibody capable of binding to an influenza virus H12N1 consists of an amino acid sequence consisting of, in an N- to C-direction, the following structural domains.

N-FR1-CDR1-FR2-CDR2-FR3-CDR3-FR4-C wherein
  FR denotes a framework region amino acid sequence and CDR denotes a complementary determining region amino acid sequence.

In the present invention, the CDR1 consists of an amino acid sequence represented by SYYMS (SEQ ID NO: 01).

In the present invention, the CDR2 consists of an amino acid sequence represented by TINTGGGSTYYADSVKG (SEQ ID NO: 02).

In the present invention, the CDR3 consists of an amino acid sequence represented by DGPYGGYDY (SEQ ID NO: 03).

Desirably, the CDR1, the CDR2, and the CDR3 are represented by SEQ ID NO: 01, SEQ ID NO: 02, and SEQ ID NO: 03, respectively. In this case, more desirably, the FR1, the FR2, the FR3, and the FR4 consist of amino acid sequences represented by EVQLVESGGGLVQPGGSL-RVSCAASGFTFS (SEQ ID NO: 04), WVRQAPGK-GLEWVS (SEQ ID NO: 05), RFTISRDNAKNTLYLQMD-SLKSEDTAVYYCAK (SEQ ID NO: 06), and WGQGTQVTVSP (SEQ ID NO: 07), respectively. In other words, it is desirable that the antibody according to the present invention consists of the following amino acid sequence.

(SEQ ID NO: 08)
EVQLVESGGGLVQPGGSLRVSCAASGFTFSSYYMSWVRQAPGKGLEW

VSTINTGGGSTYYADSVKGRFTISRDNAKNTLYLQMDSLKSEDTAVY

YCAKDGPYGGYDYWGQGTQVTVSP

The antibody consisting of the amino acid sequence represented by SEQ ID NO: 08 does not exhibit antigenic cross reactivity with regard to hemagglutinins other than influenza Hemagglutinin H12N1.

EXAMPLES

Inventive Example 1

VHH antibodies capable of binding to a hemagglutinin (hereinafter, referred to as "HA") included in an influenza virus type A H12N1 were prepared in accordance with the following procedures. In the present specification, VHH (or VHH antibody) means a variable domain of a heavy chain of a heavy chain antibody.

Immunization of Alpaca and Acquirement of Mononuclear

In order to form a VHH antibody gene library, an alpaca was immunized using recombinant HA proteins (H1, H2, H3, H4, H5, H6, H7, H8, H9, H10, H11, H12, H13, H14, H15, and H16: available from Sino Biological, catalog number: 11055-V08H) derived from an influenza virus type A H12N5 (A/green-winged teal/ALB/199/1991) as an antigen.

Specifically, the recombinant HA protein having a concentration of 100 micrograms/milliliter was administered to the alpaca. After one week, the recombinant HA protein having the same concentration was administered to the alpaca, again. In this way, the alpaca was immunized with the recombinant HA protein five times over five weeks. After another week, blood of the alpaca was extracted. Then, mononuclear cells were acquired from the blood as below.

A blood cell separation solution (available from COSMO BIO Co., Ltd., trade name: Lymphoprep) was added to a lymphocyte separation tube (available from Greiner Bio-One Co., Ltd., trade name: Leucosep). Then, the solution was subjected to centrifugation at 1,000×g under a temperature of 20 degrees Celsius for one minute.

The blood extracted from the alpaca was treated with heparin. Then, an equivalent amount of phosphate buffered saline (hereinafter, referred to as "PBS") was added to the thus-treated blood to obtain a sample solution. Then, the sample solution was added to the lymphocyte separation tube containing the blood cell separation solution.

The lymphocyte separation tube was subjected to centrifugation at 800×g under a temperature of 20 degrees Celsius for thirty minutes.

A fraction containing mononuclear cells was collected. Three times its volume of PBS was added. The fraction was subjected to centrifugation at 300×g under a temperature of 20 degrees Celsius for five minutes. The precipitate was suspended with PBS gently. After the suspending, 10 microliters of the suspension was separated in order for the count of the number of cells. The remaining suspension was subjected to centrifugation at 300×g under a temperature of 20 degrees Celsius for five minutes.

An RNA storage solution (trade name: RNAlater) having a volume of 2 milliliters was added to the precipitate. Then, the solution was suspended gently. The suspension was injected into two tubes each having a volume of 1.5 milliliters. Each tube contained 1 milliliter of the suspension. The tube was stored under a temperature of −20 degrees Celsius. The suspension (5 microliters) separated for the count of the number of cells was mixed with a Türk's solution (15 microliters), and the number of the mononuclear cells was counted with a counting chamber.

Formation of cDNA Gene Library of VHH Antibody

Then, a total RNA was extracted from the mononuclear cells, and a cDNA gene library of a VHH antibody was formed in accordance with the following procedure. In the following procedure, RNase-free-grade reagents and instruments were used.

A total RNA isolation reagent (trade name: TRIzol Regent, 1 milliliter) was added to the mononuclear cell fraction. The reagent was mixed gently with the fraction, and left at rest at room temperature for five minutes. Chloroform (200 microliters) was added to the reagent, and the reagent was shaken strongly for fifteen seconds. The reagent was left at room temperature for two-three minutes. The reagent was subjected to centrifugation at 12,000×g or less under a temperature of 4 degrees Celsius for 15 minutes.

The supernatant was moved to a new tube. RNase-free water and chloroform (200 microliters, each) were added to the tube. In addition, 500 milliliters of isopropanol was added to the tube. The liquid contained in the tube was stirred with a vortex mixer. The liquid was left at rest at room temperature for ten minutes. Then, the liquid was subjected to centrifugation at 12,000×g or less under a temperature of 4 degrees Celsius for fifteen minutes. The supernatant was removed, and the precipitate was rinsed with one milliliter of 75% ethanol. This solution was subjected to centrifugation at 7,500×g or less under a temperature of four degrees Celsius for five minutes. The solution was dried to obtain total RNA. The obtained total RNA was dissolved in RNase-free water.

In order to obtain cDNA from the total RNA, a kit including a reverse transcriptase was employed. The kit was available from Takara Bio Inc., as a trade name of PrimeScript II $1^{st}$ strand cDNA Synthesis Kit. The Random 6 mer and Oligo dT primer included in the kit were used as primers. The cDNA was obtained in accordance with the standard protocol attached to the kit.

The gene of the VHH antibody included in the alpaca was obtained from the cDNA by a PCR method. An enzyme for PCR was available from Takara Bio Inc., as a trade name of Ex-taq.

The following reagents were mixed to obtain a mixture solution.

10× buffer 5 microliters
dNTPs 4 microliters
Primer F 2 microliters
Primer R 2 microliters
cDNA template 1 microliter
Ex-taq 0.25 microliters The mixture solution was subjected to the following PCR method.

First, the mixture solution was heated at a temperature of 95 degrees Celsius for two minutes.

Then, the temperature of the mixture solution was varied in accordance with the following cycle.

Ninety six degrees Celsius for thirty seconds,
Fifty two degrees Celsius for thirty seconds, and
Sixty eight degrees Celsius for forty seconds
This cycle was repeated thirty times.

Finally, the mixture solution was heated at a temperature of sixty eight degrees Celsius for four minutes and stored at a temperature of four degrees Celsius.

The following primers were used in the present PCR method.

Primer 1:
(SEQ ID NO: 09)
5'-GGTGGTCCTGGCTGC-3'

Primer 2:
(SEQ ID NO: 10)
5'-ctgctcctcgcGGCCCAGCCGGCCatggcTSAGKTGCAGCTCGTGGAGTC-3'

Primer 3:
(SEQ ID NO: 11)
5'-TGGGGTCTTCGCTGTGGTGCG-3'

Primer 4:
(SEQ ID NO: 12)
5'-TTGTGGTTTTGGTGTCTTGGG-3'

Primer 5:
(SEQ ID NO: 13)
5'-tttgCtctGCGGCCGCagaGGCCgTGGGGTCTTCGCTGTGGTGCG-3'

Primer 6:
(SEQ ID NO: 14)
5'-tttgCtctGCGGCCGCagaGGCCgaTTGTGGTTTTGGTGTCTTGGG-3'

(Reference literature: Biomed Environ Sci., 2012; 27(2): 118-121)

Three PCR assays were conducted.

In the first PCR assay, a primer set A composed of the cDNA, Primer 1 and Primer 3 and a primer set B composed of the cDNA, Primer 1 and Primer 4 were used.

In the second PCR assay, a primer set C composed of the gene amplified with the primer set A, Primer 2, and Primer 3, and a primer set D composed of the gene amplified with the primer set B, Primer 2, and Primer 4 were used.

In the third PCR assay, a primer set E composed of the gene amplified with the primer set C, Primer 2, and Primer 5, and a primer set F composed of the gene amplified with the primer set D, Primer 2, and Primer 6 were used.

In this way, the gene library of the VHH antibody was formed. In other words, the gene library of the VHH antibody included the genes amplified with the primer sets E and F.

Formation of Phage Library

Next, a phage library was formed from the gene library of the VHH antibody in accordance of the following procedures.

Figure 1B:
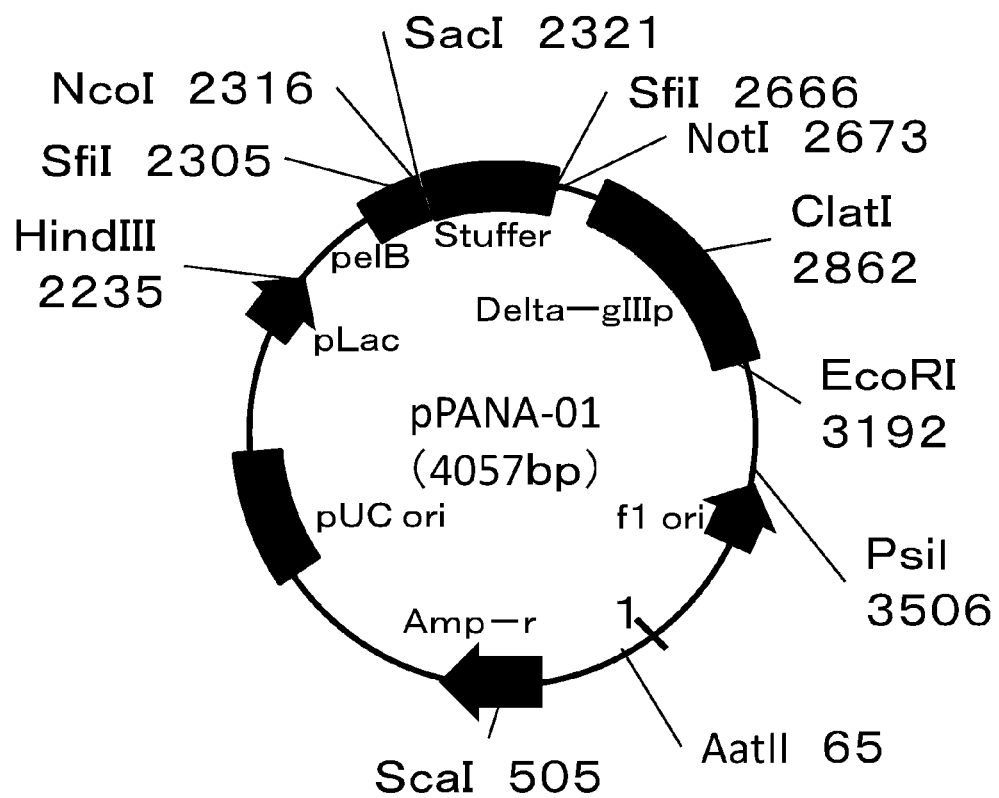
FIG. 1B shows the detail of the vector map shown in FIG. 1A.

A plasmid Vector 1 (4057 bp, see FIG. 1A) derived from a commercially available plasmid pUC119 (for example, available from Takara Bio Inc.) was treated with a restriction enzyme SfiI. The restriction enzyme site SfiI(a) consists of the gene sequence represented by GGCCCAGCCGGCC (SEQ ID NO: 15). The restriction enzyme site SfiI(b) consists of the gene sequence represented by GGCCTCTGCGGCC (SEQ ID NO: 16). FIG. 1B shows a detailed vector map of the plasmid Vector 1.

The plasmid Vector 1 consists of the following gene sequence.

(SEQ ID NO: 17)
gacgaaagggcctcgtgatacgcctatttttataggttaatgtcatg ataataatggtttcttagacgtcaggtggcacttttcggggaaatgt gcgcggaacccctatttgtttattttctaaatacattcaaatatgt atccgctcatgagacaataaccctgataaatgcttcaataatattga aaaaggaagagtatgagtattcaacatttccgtgtcgcccttattcc cttttttgcggcattttgccttcctgtttttgctcacccagaaacgc tggtgaaagtaaaagatgctgaagatcagttgggtgcacgagtgggt tacatcgaactggatctcaacagcggtaagatccttgagagttttcg ccccgaagaacgttttccaatgatgagcacttttaaagttctgctat gtggcgcggtattatcccgtattgacgccgggcaagagcaactcggt cgccgcatacactattctcagaatgacttggttgagtactcaccagt cacagaaaagcatcttacggatggcatgacagtaagagaattatgca gtgctgccataaccatgagtgataacactgcggccaacttacttctg acaacgatcggaggaccgaaggagctaaccgcttttttgcacaacat gggggatcatgtaactcgccttgatcgttgggaaccggagctgaatg aagccataccaaacgacgagcgtgacaccacgatgcctgtagcaatg gcaacaacgttgcgcaaactattaactggcgaactacttactctagc ttcccggcaacaattaatagactggatggaggcggataaagttgcag gaccacttctgcgctcggcccttccggctggctggtttattgctgat aaatctggagccggtgagcgtgggtctcgcggtatcattgcagcact ggggccagatggtaagccctcccgtatcgtagttatctacacgacgg ggagtcaggcaactatggatgaacgaaatagacagatcgctgagata ggtgcctcactgattaagcattggtaactgtcagaccaagtttactc atatatactttagattgatttaaaacttcattttttaatttaaaagga tctaggtgaagatcctttttgataatctcatgaccaaaatcccttaa cgtgagttttcgttccactgagcgtcagacccgtagaaaagatcaa aggatcttcttgagatccttttttctgcgcgtaatctgctgcttgc aaacaaaaaaaccaccgctaccagcggtggtttgtttgccggatcaa gagctaccaactctttttccgaaggtaactggcttcagcagagcgca gataccaaatactgtccttctagtgtagccgtagttaggccaccact tcaagaactctgtagcaccgcctacatacctcgctctgctaatcctg ttaccagtggctgctgccagtggcgataagtcgtgtcttaccgggtt ggactcaagacgatagttaccggataaggcgcagcggtcgggctgaa cggggggtcgtgcacacagcccagcttggagcgaacgacctacacc gaactgagatacctacagcgtgagctatgagaaagcgccacgcttcc cgaagggagaaaggcggacaggtatccggtaagcggcagggtcggaa caggagagcgcacgagggagcttccaggggggaaacgcctggtatctt tatagtcctgtcgggtttcgccacctctgacttgagcgtcgatttt gtgatgctcgtcaggggggcggagcctatggaaaaacgccagcaacg cggccttttacggttcctggccttttgctggccttttgctcacatg ttctttcctgcgttatcccctgattctgtggataaccgtattaccgc ctttgagtgagctgataccgctcgccgcagccgaacgaccgagcgca gcgagtcagtgagcgaggaagcggaagagcgcccaatacgcaaaccg -continued

```
cctctcccgcgcgttggccgattcattaatgcagctggcacgacag gtttcccgactggaaagcgggcagtgagcgcaacgcaattaatgtga gttagctcactcattaggcaccccaggctttacactttatgcttccg gctcgtatgttgtgtggaattgtgagcggataacaatttcacacagg aaacagctatgaccatgattacgccAAGCTTCGAAGGAGACAGTCAT Aatgaaatacctgctgccgaccgctgctgctggtctgctgctcctcg cGGCCCAGCCGGCCatggagcTCAAGATGACACAGACTACATCCTCC

CTGTCAGCCTCTCTGGGAGACAGAGTCACCATCAGTTGCAGGGCAAG

TCAGGACATTAGCGATTATTTAAACTGGTATCAGCAGAAACCAGATG

GAACTGTTAAACTCCTGATCTATTACACATCAAGTTTACACTCAGGA

GTCCCATCAAGGTTCAGTGGCGGTGGGTCTGGAACAGATTATTCTCT

CACCATTAGCAACCTGGAGCAAGAAGATATTGCCACTTACTTTTGCC

AACAGGGTAATACGCTTCCGTGGACGTTTGGTGGAGGCACCAAGCTG

GAAATCAAACGGGCTGATGCTGCACCAACTgtaGGCCtctGCGGCCG

CagaGcaaaaactcatctcagaagaggatctgaatggggccgcaTAG ggttccggtgattttgattatgaaaagatggcaaacgctaataaggg ggctatgaccgaaaatgccgatgaaaacgcgctacagtctgacgcta aaggcaaacttgattctgtcgctactgattacggtgctgctatcgat ggtttcattggtgacgtttccggccttgctaatggtaatggtgctac tggtgattttgctggctctaattcccaaatggctcaagtcggtgacg gtgataattcacctttaatgaataatttccgtcaatatttaccttcc ctccctcaatcggttgaatgtcgccttttgtctttagcgctggtaa accatatgaattttctattgattgtgacaaaataaacttattccgtg gtgtctttgcgtttcttttatatgttgccacctttatgtatgtattt tctacgtttgctaacatactgcgtaataaggagtctTAATAAgaatt cactggccgtcgttttacaacgtcgtgactgggaaaaccctggcgtt acccaacttaatcgccttgcagcacatccccctttcgccagctggcg taatagcgaagaggcccgcaccgatcgcccttcccaacagttgcgca gcctgaatggcgaatggcgcctgatgcggtattttctccttacgcat ctgtgcggtatttcacaccgCATATGaAAATTGTAAgcgttaatatt ttgttaaaattcgcgttaaattttgttaaatcagctcattttttaa ccaataggccgaaatcggcaaaatcccttataaatcaaaagaataga ccgatagggttgagtgttgttccagtttggaacaagagtccacta ttaaagaacgtggactccaacgtcaaagggcgaaaaaccgtctatca gggcgatggcccactacgtgaaccatcaccctaatcaagttttttgg ggtcgaggtgccgtaaagcactaaatcggaacctaaagggagccc cgatttagagcttgacggggaaagccggcgaacgtggcgagaaagga agggaagaaagcgaaaggagcgggcgctagggcgctggcaagtgtag cggtcacgctgcgcgtaaccaccacccgccgcgcttaatgcgccg ctacaGGGCGCGTcccatATGgtgcactctcagtacaatctgctctg atgccgcatagttaagccagccccgacacccgccaacacccgctgac
```

-continued

```
gcgccctgacgggcttgtctgctcccggcatccgcttacagacaagc tgtgaccgtctccgggagctgcatgtgtcagaggttttcaccgtcat caccgaaacgcgcga
```

Similarly, the gene library of the VHH antibody was treated with the restriction enzyme Sfil. In this way, VHH antibody gene fragments were obtained.

The thus-treated plasmid Vector 1 was mixed with the VHH antibody gene fragments at a ratio of 1:2. An enzyme (available from Toyobo Co. Ltd., trade name: Ligation High ver. 2) was injected into the mixture solution. The mixture solution was left at rest at a temperature of 16 degrees Celsius for two hours. In this way, each of the VHH antibody gene fragments was ligated into the plasmid Vector 1.

Coli bacteria (available from Takara Bio Inc., trade name: HST02) were transfected with the thus-ligated plasmid Vector 1.

Then, the coli bacteria were incubated for fifteen hours on a 2YT plate culture medium containing ampicillin at a concentration of 100 micrograms/milliliter. In this way, obtained was a library of phages each of which displays a protein obtained from the gene fragment included in the gene library of the VHH antibody.

After the incubation, a concentration of the library was calculated by counting the number of single colonies formed on the 2YT plate culture medium. As a result, the library of the phages had a concentration of 2.6E+8/milliliter.

Biopanning

VHH antibodies capable of specifically binding to the HA protein were obtained from the phage library in accordance with the following procedures.

In order to extract the clones each capable of binding to the antigen from among the phages which expressed the VHH antibody, biopanning was conducted twice.

Coli bacteria (HST02) to which the VHH antibody gene fragment included in the gene library of the VHH antibody had been introduced were incubated at a temperature of 30 degrees Celsius in the 2YT AG culture medium containing 100 micrograms/milliliter of ampicillin and 1% glucose until a value $OD_{600}$ indicating absorbance reached 1.0. The 2YT AG culture medium had a volume of 100 milliliters. In this way, the coli bacteria were proliferated.

Helper phages (available from Invitrogen company, trade name: M13K07) were added to the coli bacteria culture medium in such a manner that the multiplicity of infection (hereinafter, referred to as "MOI") was approximately twenty.

Then, the culture medium was warmed for about thirty minutes at a temperature of 37 degrees Celsius. Then, the culture medium was subjected to centrifugation at a rotation speed of 4000 rpm for ten minutes to collect the coli bacteria. The coli bacteria were incubated overnight at a temperature of 30 degrees Celsius in a 2YTAK culture medium containing 100 micrograms/milliliter of ampicillin and 50 micrograms/milliliter of kanamycin, while subjected to centrifugation at 213 rpm.

The incubation liquid (100 milliliters) containing the thus-incubated coli bacteria was injected into two centrifugation tubes (volume: 50 milliliters, each). The two centrifugation tubes were subjected to centrifugation for ten minutes at a rotation speed of 4,000 rpm. Then, the supernatants (20 milliliters, each) were collected.

The supernatants (40 milliliters) were added to a 20% polyethylene glycol solution (10 milliliters) containing NaCl (2.5 M). Then, the mixture solution was inverted and mixed. Subsequently, the mixture solution was cooled on ice for approximately one hour. The mixture was subjected to centrifugation for ten minutes at a rotation speed of 4,000 rpm. Then, the supernatant was removed. PBS containing 10% glycerol was injected toward the precipitate. Finally, the precipitate was loosened and dissolved. In this way, a library of phages each of which displays the VHH antibody was obtained.

Screening of VHH Antibody Capable of Specifically Binding to HA (A) Immobilization of HA Antigen HA was mixed with PBS to prepare an HA solution. The concentration of HA was 10 micrograms/milliliter. The HA solution (2 milliliters) was injected into an immunotube (available from NUNC Co. Ltd.). The HA solution was left at rest in the immunotube for one hour. In this way, HA was immobilized in the immunotube.

Then, the inside of the immunotube was washed three times with PBS.

The inside of the immunotube was filled with PBS which contained 3% skim milk (available from Wako Pure Chemical Industries, Ltd.). In this way, HA was blocked as an antigen in the immunotube.

The immunotube was left at rest at room temperature for one hour. Subsequently, the inside of the immunotube was washed three times with PBS.

(B) Panning

The library of the phages each of which displays the VHH antibody (concentration: approximately 10E+11/milliliter) was mixed with 2 milliliters of PBS containing 3% skim milk to prepare a mixture solution. The mixture solution was injected into the immunotube in which the HA antigen was immobilized.

The immunotube was provided with a lid formed of Parafilm. Then, the immunotube was rotated upside down in a rotator for ten minutes.

The immunotube was left at rest at room temperature for one hour.

The inside of the immunotube was washed ten times with PBS containing 0.05% Tween 20. Hereinafter, such PBS is referred to as "PBST".

The inside of the immunotube was filled with PBST. Subsequently, the immunotube was left at rest for ten minutes. Then, the inside of the immunotube was washed ten times with PBST.

In order to extract phages each of which displays the VHH antibody bound to the HA antigen, 100 mM trimethylamine solution (1 milliliter) was injected into the immunotube.

The immunotube was provided with a lid formed of Parafilm. Then, the immunotube was rotated upside down in a rotator for ten minutes.

In order to neutralize the solution, the solution was moved to a tube containing 1 mL of 0.5 M Tris/HCl (pH: 6.8). Again, the extraction of the phage was repeated using a 100 mM trimethylamine solution (1 milliliter). In this way, 3 mL of an extraction liquid was obtained.

The extraction liquid (1 mL) was mixed with 9 mL of *coli* bacteria HST02. The mixture solution was left at rest for one hour at a temperature of 30 degrees Celsius.

In order to count the number of colonies, 10 microliters of the mixture solution containing the *coli* bacteria HST02 was distributed onto a small plate containing a 2TYA culture medium (10 milliliters/plate).

The rest of the mixture solution was subjected to centrifugation. The supernatant was removed, and the precipitate was distributed onto a large plate containing a 2TYA culture medium (40 milliliters/plate). These two plates were left at rest overnight at a temperature of 30 degrees Celsius. In this way, first panning was conducted.

Second panning was conducted identically to the procedure of the first panning. In other words, the panning was repeated. In this way, the monoclonal phages on which the VHH antibody was displayed were purified.

After the second panning, a colony of the *coli* bacteria was picked up with a toothpick. The picked-up one colony was put onto one well of 96-flat-bottom plate. This was repeated. One well contained 200 microliters of a 2YTAG culture medium.

The solutions contained in the wells were stirred at a rotation speed of 213 rpm at a temperature of 30 degrees Celsius.

The solution (50 microliters) containing grown *coli* bacteria was collected. The collected solution was mixed with 50 microliters of a 2YTA culture medium contained in a plate. The 2YTA culture medium contained helper phages such that the multiplicity of infection (i.e., MOI) was set to be 20. The solution was left at rest at a temperature of 37 degrees Celsius for forty minutes.

The plate containing the 2YTA culture medium was subjected to centrifugation at 1,800 rpm for twenty minutes. The supernatant was removed. The precipitate contained the *coli* bacteria. The precipitate was mixed with 200 microliters of a 2YTAK culture medium. The mixture solution was left at rest overnight at a temperature of 30 degrees Celsius.

The mixture solution was subjected to centrifugation at 1800 rpm for twenty minutes. The supernatant containing the *coli* bacteria was collected.

(C) Qualitative Evaluation of Phage-Displayed VHH Antibody and Antigen by ELISA

An HA protein solution having a concentration of 100 micrograms/milliliter was injected as an antigen into each of the wells of a 96-well plate (available from Thermo Fisher Scientific K.K., trade name: maxisorp). The volume of the HA protein solution in each well was 50 microliters. The 96-well plate was left at rest at room temperature for one hour. In this way, the HA antigen was immobilized in each well.

Each of the wells was washed with PBS three times. Then, PBS containing 3% skim milk (available from Wako Pure Chemical Industries, Ltd.) was injected into each well (200 microliters/well). The 96-well plate was left at rest at room temperature for one hour. In this way, the HA protein was blocked in each well. Subsequently, each well was washed three times with PBS.

The monoclonal phages each of which displays the VHH antibody were injected into each well (50 microliters/well). Then, the 96-well plate was left at rest for one hour. In this way, the phages reacted with the HA antigen.

Each well was washed three times with PBST. Then, an anti-M13 antibody (available from ABCAM company, trade name: ab50370, 10,000-fold dilution) was injected into each well (50 microliters/well). Then, each well was washed three times with PBST.

A color-producing agent (available from Thermo Scientific, trade name: 1-step ultra TMB-ELISA) was injected into each well (50 microliters/well). The 96-well plate was left at rest for two minutes to cause the color-producing agent to react with the antibody.

A sulfuric acid aqueous solution (normal, i.e., 1 N) was injected into each well at a concentration of 50 microliters/well to cease the reaction.

The absorbance of the solution at a wavelength of 450 nanometers was measured.

Six wells each having good absorbance measurement result were selected. The DNA sequences included in the phages contained in the selected six wells were analyzed by Greiner Company. The analysis results of the DNA sequences will be described below. The following one DNA sequence was found.

(SEQ ID NO: 18)
GAGGTGCAGCTCGTGGAGTCTGGGGGAGGCTTGGTGCAGCCTGGGGG

GTCTCTGAGAGTCTCCTGTGCAGCCTCTGGATTCACCTTCAGTAGCT

ACTACATGAGCTGGGTCCGCCAGGCTCCAGGGAAGGGGCTCGAGTGG

GTCTCAACTATTAATACTGGTGGTGGTAGCACATACTATGCAGACTC

CGTGAAGGGCCGATTCACCATCTCCAGAGACAACGCCAAGAACACCC

TCTATCTGCAAATGGACAGTCTGAAATCTGAAGATACAGCCGTGTAT

TATTGTGCAAAAGATGGGCCATATGGCGGGTACGACTACTGGGGCCA

GGGGACCCAGGTCACCGTCTCCCCA

The protein synthesized from the DNA sequence represented by SEQ ID NO: 18 consists of the following amino acid sequence.

(SEQ ID NO: 08)
EVQLVESGGGLVQPGGSLRVSCAASGFTFSSYYMSWVRQAPGKGLEW

VSTINTGGGSTYYADSVKGRFTISRDNAKNTLYLQMDSLKSEDTAVY

YCAKDGPYGGYDYWGQGTQVTVSP

Expression of Anti-H12N1 VHH Antibody

Figure 2:
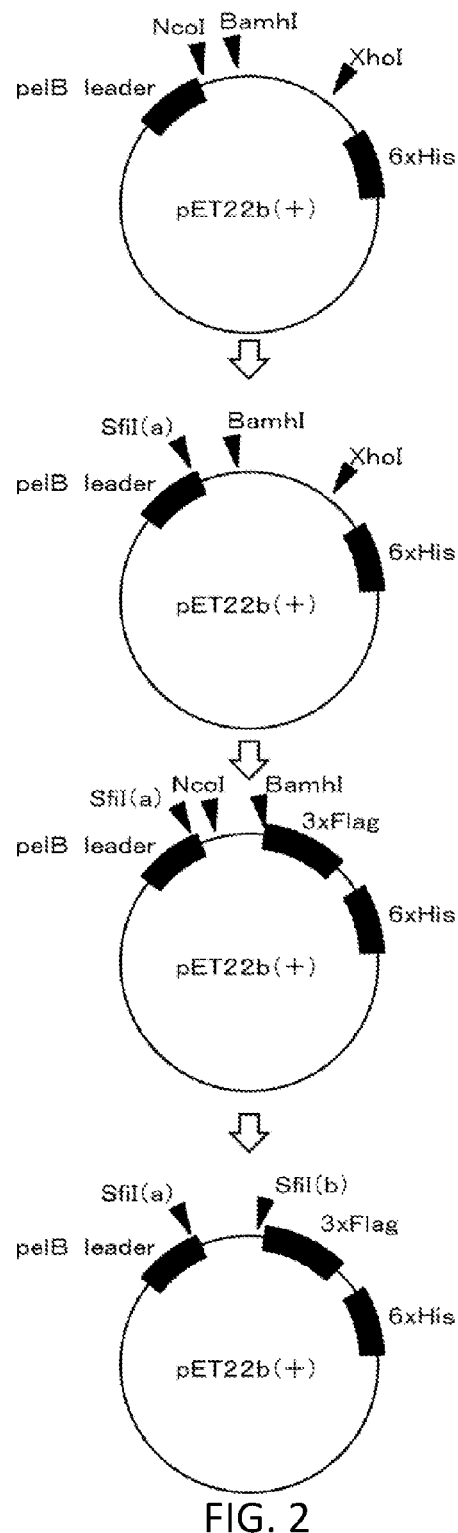
FIG. 2 shows a synthesis procedure of a vector used to express the VHH antibody.
Figure 3A:
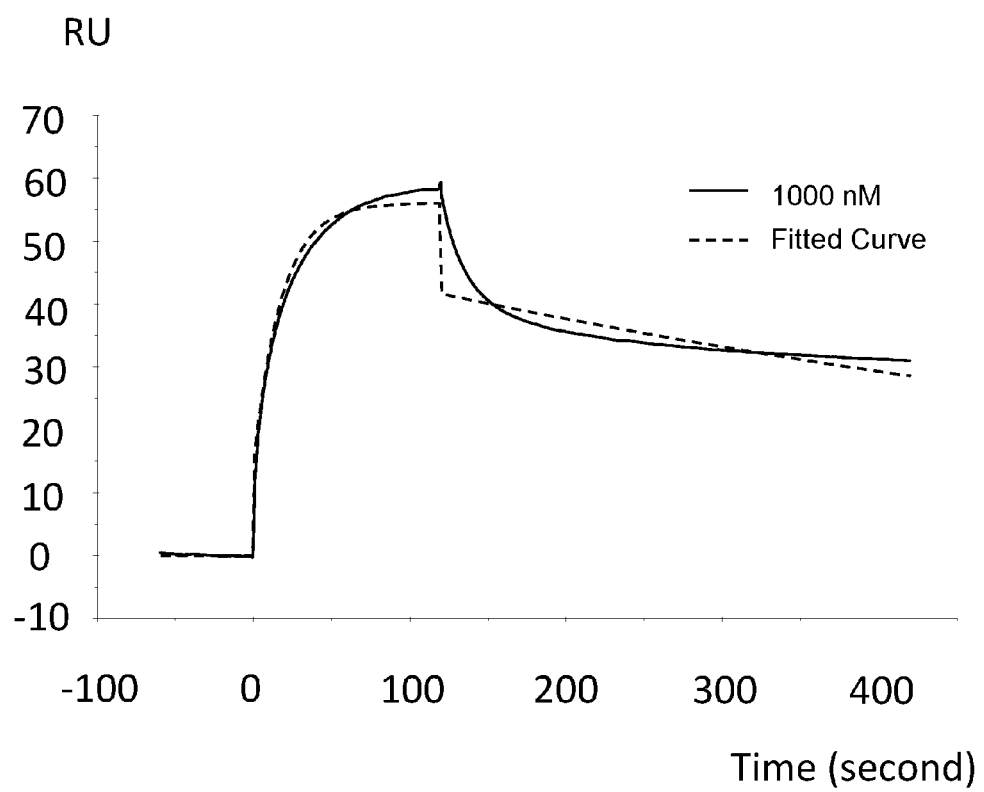
FIG. 3A is a graph showing the evaluation result obtained from the SPR evaluation device T200 for 1,000 nM of the anti-H12N1 antibody.
Figure 3B:
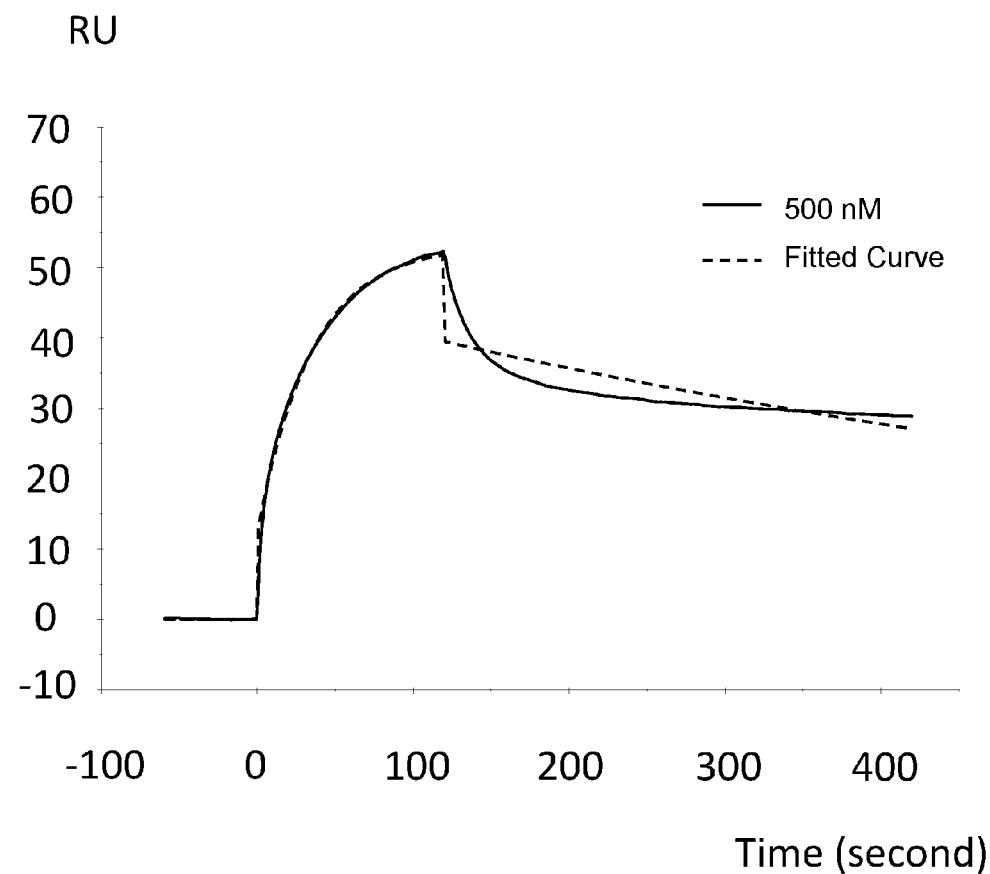
FIG. 3B is a graph showing the evaluation result obtained from the SPR evaluation device T200 for 500 nM of the anti-H12N1 antibody.
Figure 3C:
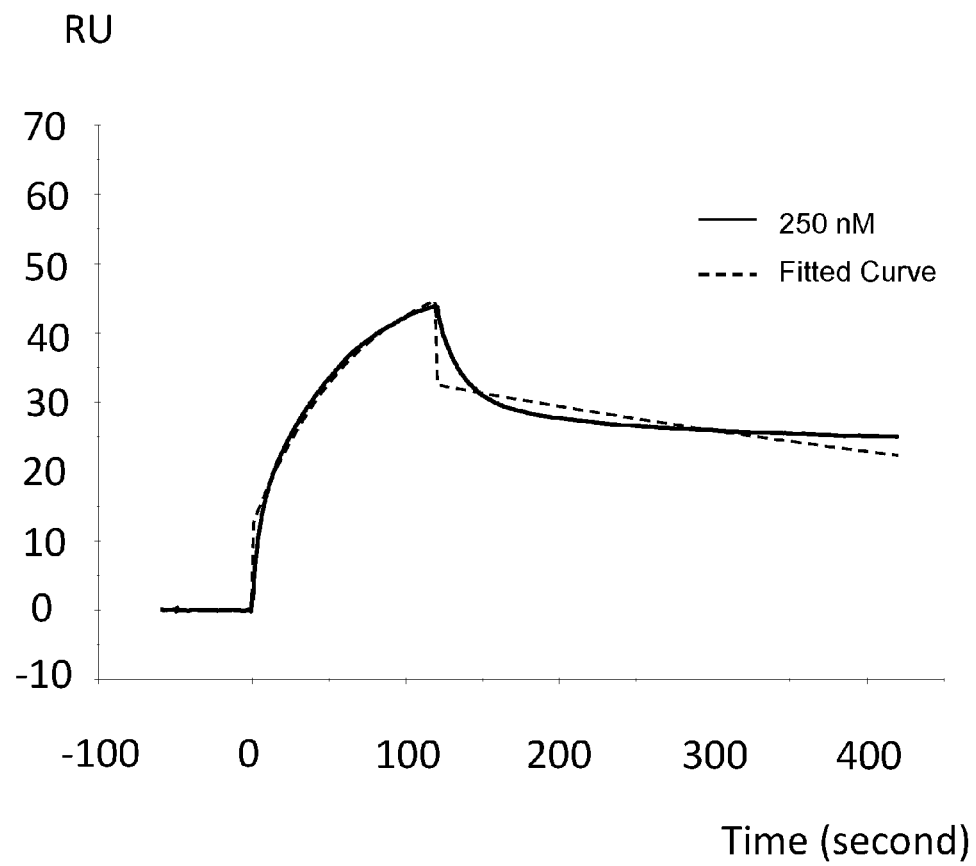
FIG. 3C is a graph showing the evaluation result obtained from the SPR evaluation device T200 for 250 nM of the anti-H12N1 antibody.
Figure 3D:
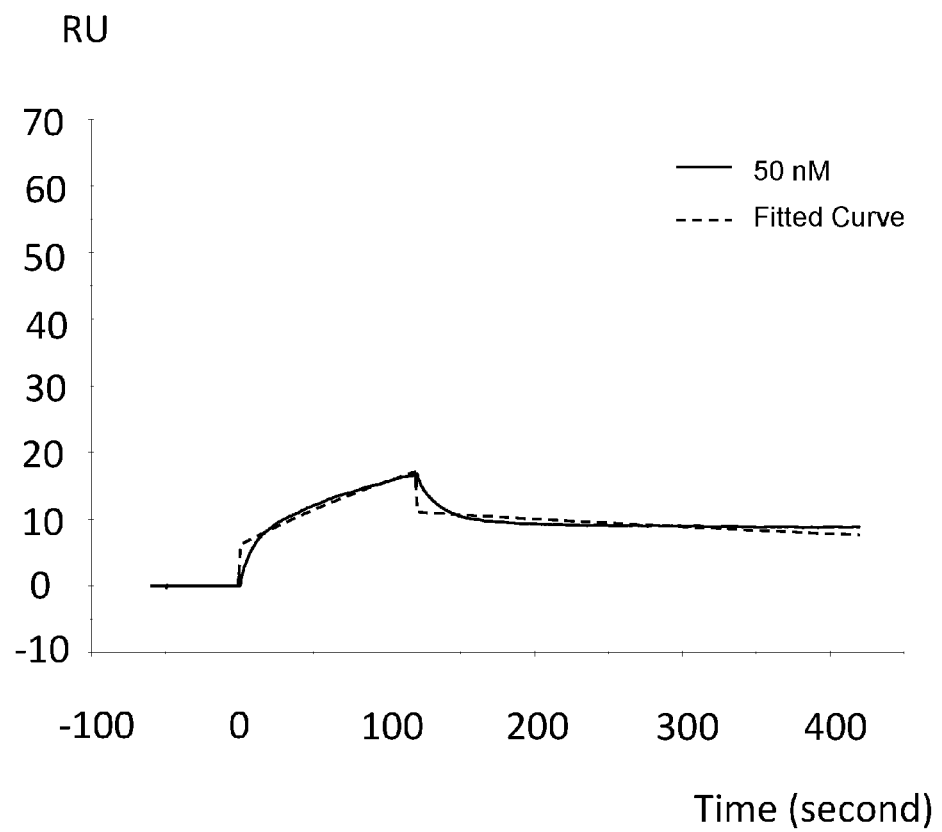
FIG. 3D is a graph showing the evaluation result obtained from the SPR evaluation device T200 for 50 nM of the anti-H12N1 antibody.
Figure 3E:
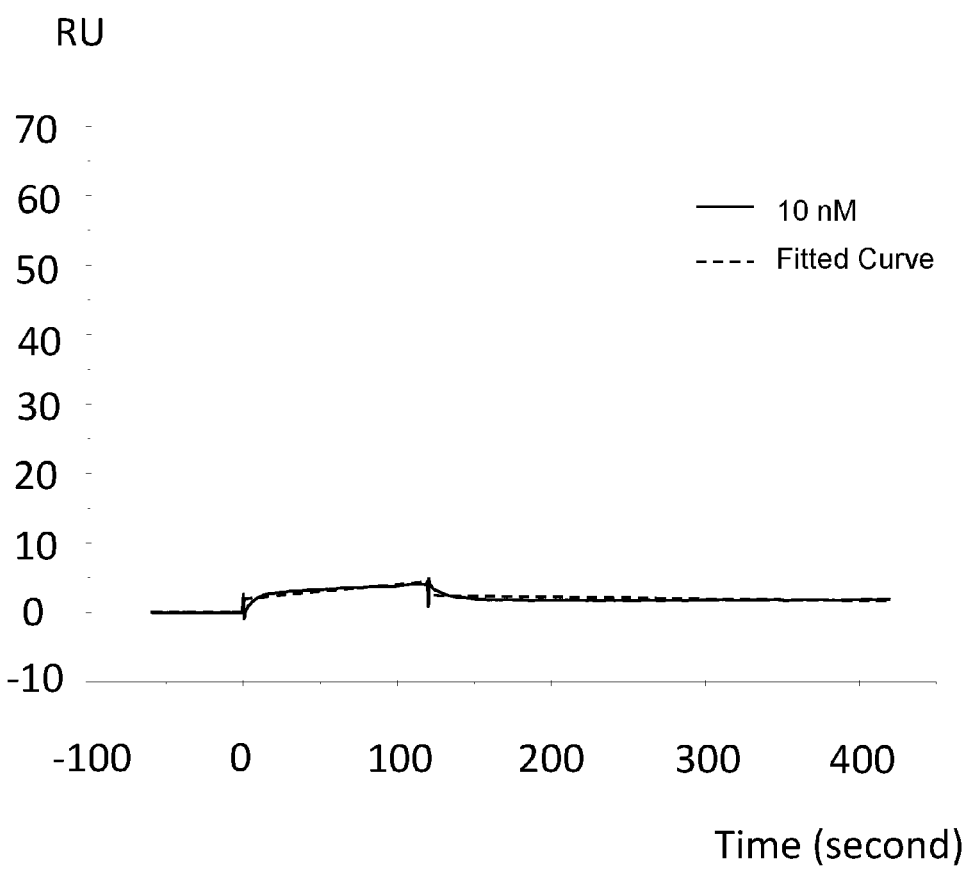
FIG. 3E is a graph showing the evaluation result obtained from the SPR evaluation device T200 for 10 nM of the anti-H12N1 antibody.
Figure 3F:
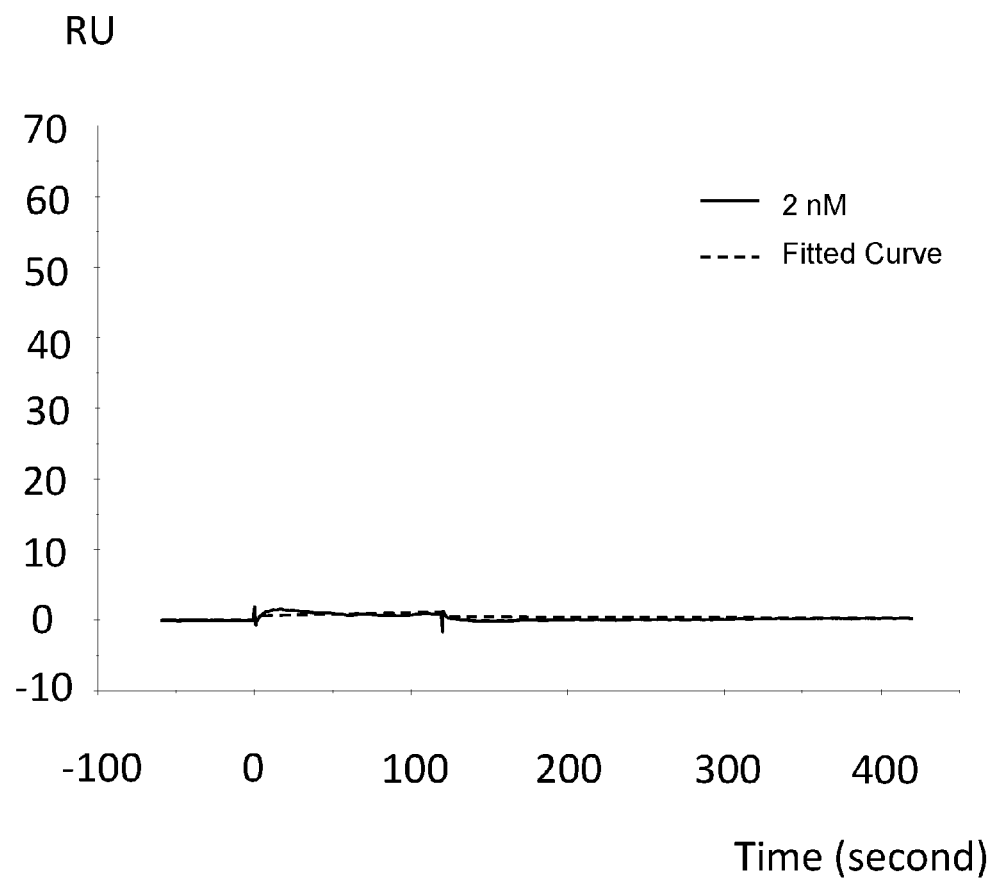
FIG. 3F is a graph showing the evaluation result obtained from the SPR evaluation device T200 for 2 nM of the anti-H12N1 antibody.
Figure 4:
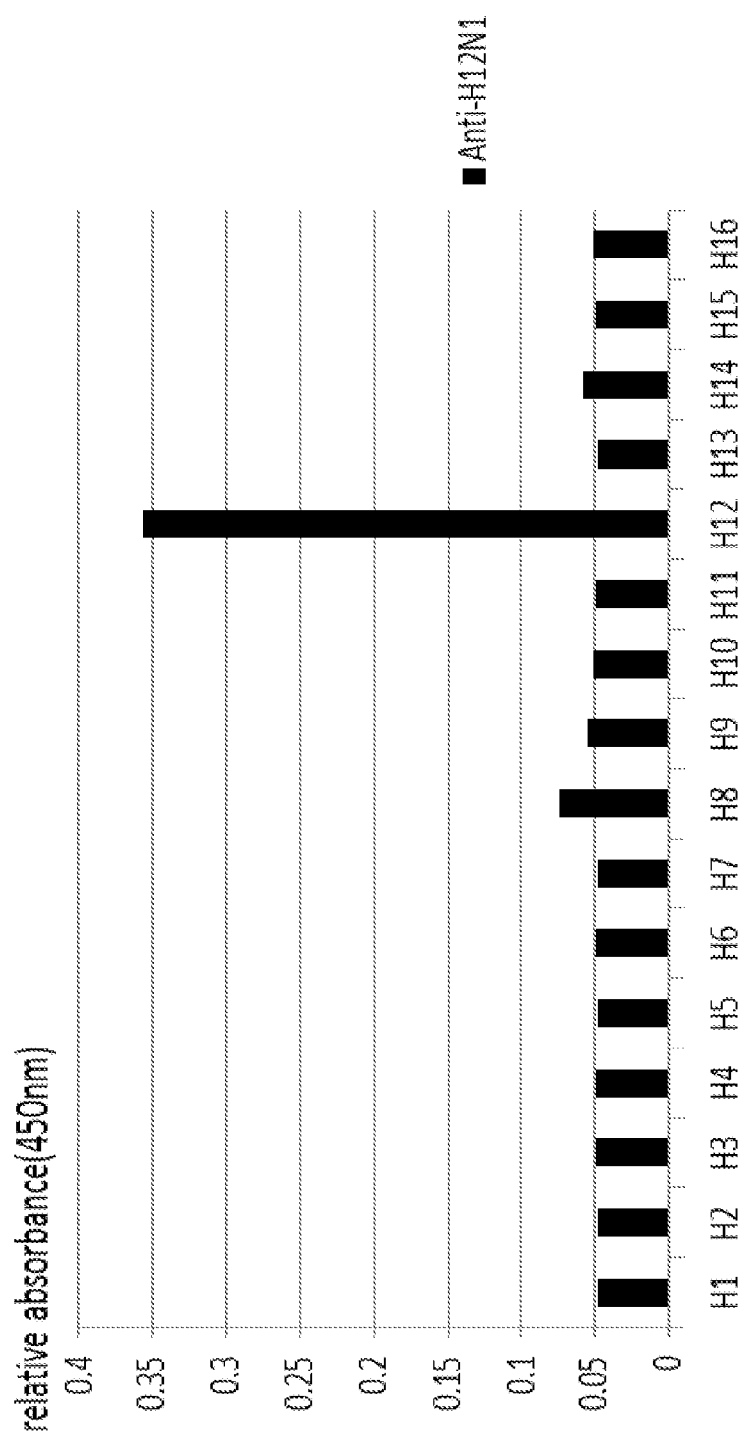
FIG. 4 is a graph showing an absorbance measurement result of a solution containing the VHH antibody consisting of the amino acid sequence represented by SEQ ID NO: 08 at a wavelength of 450 nanometers to all hemagglutinin subspecies.

A vector pET22b(+) was purchased from Merck Millipore Company. Using PrimeStar Mutagenesis Basal Kit (available from Takara Bio Inc.), a 3xFlag tag and two restriction enzyme sites Sfil(a) and Sfil(b) were added to the vector pET22b(+) by a PCR method. See FIG. 2. The procedure shown in FIG. 2 will be described below in more detail.

First, the restrict ion enzyme site Sfil(a) was add to the vector pET22b(+) by a PCR method using the following two primers and a restrict ion enzyme (available from Takara Bio Inc., trade name: PrimeSTAR Max DNA polymerase).

Primer 1:
(SEQ ID NO: 19)
5'-GCCGGCTGGGCcGCGAGGAGCAGCAGACCA-3'

Primer 2:
(SEQ ID NO: 20)
5'-GCCCAGCCGGCcATGGCCATGGATATCGGA-3'

Then, a 3xFlag tag DNA fragment having restriction enzyme sites Bamhl and Xhol at 5'-terminal end and 3'-terminal end, respectively, was formed using the following two primers and restriction enzymes (available from Takara Bio Inc., trade name: PrimeSTAR Max DNA polymerase).

Primer 1:
(SEQ ID NO: 21)
5'-CATGGATATCGGAATTAATTCggatccGACTACAAAGACCATGA

CGGTGATTATAAAGATCATGACATCctcgagCACCACCACCACCACC

ACTGA-3'

Primer 2:
(SEQ ID NO: 22)
5'-TCAGTGGTGGTGGTGGTGGTGctcgagGATGTCATGATCTTTAT

AATCACCGTCATGGTCTTTGTAGTCggatccGAATTAATTCCGATAT

CCATG-3'

This 3xFlag tag DNA fragment and the vector pET22b(+) were treated with two restriction enzymes Bamhl and Xhol (available from Takara Bio Inc.)

The 3xFlag tag DNA fragment was ligated into the vector pET22b(+) using Ligation Kit (available from Takara Bio Inc.). In this way, obtained was the vector pET22b(+) to which the 3xFlag tag and the restriction enzyme site Sfil(a) were added.

A DNA fragment having restriction enzyme sites Ncol and Bamhl at 5'-terminal end and 3'-terminal end, respectively, was formed using the following two primers and restriction enzymes (available from Takara Bio Inc., trade name: PrimeSTAR Max DNA polymerase).

Primer 1:
(SEQ ID NO: 23)
5'-AAATACCTGCTGCCGccatggATATCGGAATTAATTCggcctct gcggccGCAggatccGACTACAAAGACCAT-3'

Primer 2:
(SEQ ID NO: 24)
5'-ATGGTCTTTGTAGTCggatccTGCggccgcagaggccGAATTAA

TTCCGATATCcatggCGGCAGCAGGTATTT-3'

Then, this DNA fragment and the vector pET22b(+) were treated with two restriction enzymes Ncol and Bamhl (available from Takara Bio Inc.)

This DNA fragment was ligated into the vector pET22b (+) using Ligation Kit (available from Takara Bio Inc.). In this way, obtained was the vector pET22b(+) to which the 3xFlag tag and the restriction enzyme sites Sfil(a) and Sfil(b) were added.

The sequence of the vector pET22b(+) was analyzed by Greiner Company. For the analysis of the sequence, a general T7 promotor primer set was used.

Selected were the vectors pET22b(+) which were confirmed through the analysis of the sequence to have been formed as planned.

Vectors pET22b(+) included in the liquid obtained by the PCR method were purified and collected in 50 microliters of diluted water using a DNA extraction kit (available from Promega KK). The thus-collected vectors pET22b(+) was treated with the Sfil restriction enzyme.

On the other hand, the plasmid Vector 1 into which the VHH antibody gene fragment included in the gene library of the VHH antibody was ligated was treated with the Sfil restriction enzyme. In this way, obtained were the following DNA (SEQ ID NO: 25) including the gene sequence coding for the amino acid sequence represented by SEQ ID NO: 08.

(SEQ ID NO: 25)
5'-GGCCCAGCCGGCCATGGCTGAGGTGCAGCTCGTGGAGTCTGGGG

GAGGCTTGGTGCAGCCTGGGGGGTCTCTGAGAGTCTCCTGTGCAGCC

TCTGGATTCACCTTCAGTAGCTACTACATGAGCTGGGTCCGCCAGGC

TCCAGGGAAGGGGCTCGAGTGGGTCTCAACTATTAATACTGGTGGTG

GTAGCACATACTATGCAGACTCCGTGAAGGGCCGATTCACCATCTCC

AGAGACAACGCCAAGAACACCCTCTATCTGCAAATGGACAGTCTGAA

ATCTGAAGATACAGCCGTGTATTATTGTGCAAAAGATGGGCCATATG

GCGGGTACGACTACTGGGGCCAGGGGACCCAGGTCACCGTCTCCCCA

GCGCACCACAGCGAAGACCCCACGGCCTCTGCGGCCGCAGGATCCGA

CTACAAAGACCATGACGGTGATTATAAAGATCATGACATCGATTACA

AAGATGACGATGACAAACTCGAGCACCACCACCACCACCACTGATCT

GCGGCC-3'

The DNA was treated with the Sfil restriction enzyme. Then, the thus-treated DNA was collected by an electrocataphoresis method. Using a DNA ligation set (available from Takara Bio Inc.), the collected DNA (SEQ ID NO: 26) was ligated into the plasmid treated with the Sfil restriction enzyme.

(SEQ ID NO: 26)
5'-CGGCCATGGCTGAGGTGCAGCTCGTGGAGTCTGGGGGAGGCTTG

GTGCAGCCTGGGGGGTCTCTGAGAGTCTCCTGTGCAGCCTCTGGATT

CACCTTCAGTAGCTACTACATGAGCTGGGTCCGCCAGGCTCCAGGGA

AGGGGCTCGAGTGGGTCTCAACTATTAATACTGGTGGTGGTAGCACA

TACTATGCAGACTCCGTGAAGGGCCGATTCACCATCTCCAGAGACAA

CGCCAAGAACACCCTCTATCTGCAAATGGACAGTCTGAAATCTGAAG

ATACAGCCGTGTATTATTGTGCAAAAGATGGGCCATATGGCGGGTAC

GACTACTGGGGCCAGGGGACCCAGGTCACCGTCTCCCAGCGCACCA

CAGCGAAGACCCCACGGCCTCTGCGGCCGCAGGATCCGACTACAAAG

ACCATGACGGTGATTATAAAGATCATGACATCGATTACAAAGATGAC

GATGACAAACTCGAGCACCACCACCACCACCACTGATCTG-3'

The ligation solution (2.5 microliters) and *coli* bacteria DH5α (available from Nippon Gene, 25 microliters) were mixed on ice. The mixture solution was left at rest on the ice for six minutes. Then, the mixture solution was heated at a temperature of 42 degrees Celsius for forty five seconds. Finally, the mixture solution was left at rest on the ice for one minute. This procedure is known as a general heat shock method.

The total amount of the mixture solution was distributed onto a LBA culture medium containing ampicillin at a concentration of 100 micrograms/milliliter. The LBA culture medium was left at rest overnight at a temperature of 37 degrees Celsius.

Three colonies were selected from among the colonies formed on the LBA culture medium. The selected three colonies were incubated in the LBA culture medium (3 milliliters) overnight.

The plasmids contained in the incubated *coli* bacteria were extracted from the LBA culture medium using a plasmid extract ion kit (available from QIAGEN, trade name: QIAprepspin miniprep kit) In order to confirm that the gene of the targeted VHH antibody was inserted in the plasmid, the sequence of the plasmid was analyzed by Greiner Company. For the analysis of the sequence, a general T7 promotor primer set was used.

Selected were plasmids which were confirmed through the analysis of the sequence to have been formed as planned.

*Coli* bacteria (Competent Cell BL21 (DE3) pLysS, available from Life technologies Company) were transfected with the selected plasmids by a heat shock method.

An SOC culture medium (50 microliters) was injected into the solution containing the transfected *coli* bacteria. Then, the *coli* bacteria were rescued at a temperature of 37 degrees Celsius for one hour, while shaken at 213 rpm.

Then, the *coli* bacteria solution was collected. The collected *coli* bacteria solution (5 milliliters) was distributed onto a LBA culture medium. The LBA culture medium was left at rest overnight at a temperature of 37 degrees Celsius.

One colony was selected from among the colonies formed in the LBA culture medium. The selected colony was picked up with a toothpick. The picked-up colony was incubated in a LBA culture medium (3 milliliters) at a temperature of 37 degrees Celsius, while shaken at 213 rpm. In this way, a culture liquid was obtained.

In addition, the culture liquid (25 milliliters) was mixed with a LBA culture medium (500 milliliters). Until the absorbance of the mixture solution at a wavelength of 600 nanometers reached 0.5, the mixture solution was shaken at 160 rpm at a temperature of 37 degrees Celsius.

After the absorbance reached 0.5, an isopropylthiogalactoside solution (hereinafter, referred to as "IPTG solution") was added to the mixture solution. The final concentration of the IPTG solution was 1 mM. The *coli* bacteria contained in the mixture solution were incubated at a temperature of 37 degrees Celsius for six hours. In order to collect the thus-incubated *coli* bacteria, the mixture solution was subjected to centrifugation at 6,000 rpm for ten minutes at a temperature of 4 degrees Celsius.

The collected *coli* bacteria were mixed with ten times its volume of PBS. The mixture solution was stirred with a vortex mixer. In this way, the *coli* bacteria were washed. Then, the mixture solution was subjected to centrifugation at 6,000 rpm for ten minutes at a temperature of 4 degrees Celsius to collect *coli* bacteria. The collected *coli* bacteria were mixed again with ten times its volume of PBS. The *coli* bacteria contained in the mixture solution were disintegrated with an ultrasonic wave.

The disintegration liquid containing *coli* bacteria was subjected to centrifugation at 10,000 rpm for fifteen minutes at a temperature of 4 degrees Celsius. The supernatant was collected. The collected supernatant was filtered through a 0.45-micrometer filter.

The filtrate was purified with His-trap (available from GE Healthcare) in accordance with the recommended protocol. In the purification, an elution buffer having a total amount of 3 microliters was used for 1 milliliter of the filtrate. The buffer solution contained in the filtrate was substituted with PBS, using PD-10 (available from GE Healthcare). In the substitution, PBS having a total amount of 2.5 microliters was used for 1 milliliter of the filtrate. In this way, a solution containing the anti-H12N1 antibody was obtained.

The anti-H12N1 antibody contained in the thus-obtained solution was quantified with an absorption spectrometer (available from Scrum Inc., trade name: nanodrop) on the basis of the abs of 280 nanometers. As a result, the concentration of the anti-H12N1 antibody was 4 milligrams/milliliter.

(D-1) Surface Plasmon Resonance Evaluation of Anti-H12N1 Antibody Using Recombinant HA The anti-H12N1 antibody was evaluated as below using a recombinant HA and a surface plasmon resonance evaluation device. The details of the surface plasmon resonance (hereinafter, referred to as "SPR") will be described below.

SPR evaluation device: T200 (available from GE Healthcare)

Immobilization buffer: HBS-EP (available from GE Healthcare)

Running buffer: HBS-EP+ (available from GE Healthcare)

Sensor chip: CM5 (available from GE Healthcare)

Immobilization reagents: N-hydroxysuccinimide (NHS) and N-[3-(dimethylamino)propyl]-N'-ethylcarbodiimide (EDC)

H12: recombinant hemagglutinin (HA) protein derived from influenza virus subtype A H12N5 (available from Sino Biological Inc., trade name: 17718-V08H)

H12 was immobilized in accordance with the wizard included in the control software of the SPR evaluation device T200. For the immobilization of H12, an acetic acid solution having a pH of 5.0 was used. The acetic acid solution had a concentration of 1 microgram/milliliter. The immobilization amount was set to be 200 RU.

The anti-H12N1 antibody consisting of the amino acid sequence represented by SEQ ID NO: 08 was used as an analyte. In the first to fourth analyses, the concentrations of the anti-H12N1 antibody contained in the running buffer were adjusted to 1000 nM, 500 nM, 250 nM, 50 nM, 10 nM and 2 nM, respectively. FIG. 3A-FIG. 3F are graphs showing the evaluation result obtained from the SPR evaluation device T200 for each concentrations of the anti-H12N1 antibody. The dissociation constant Kd was calculated using the evaluation software (available from GE Healthcare). As a result, the dissociation constant Kd was 22.8 nM.

(D-2) Evaluation of Cross Reactivity to Other Influenza Virus Subtypes by ELISA

The binding ability of the VHH antibody consisting of the amino acid sequence represented by SEQ ID NO: 08 to the HA protein was evaluated by an ELISA measurement method.

Prepared was a solution containing the VHH #20 consisting of the amino acid sequence represented by SEQ ID NO: 08 at a concentration of 1 microgram/milliliter in 3% skim milk PBS. Hereinafter, this solution is referred to as "Solution A".

Each PBS solution containing one hemagglutinin (H1, H2, H3, H4, H5, H6, H7, H8, H9, H10, H11, H12, H13, H14, H15 or H16, at a concentration of 1 microgram/milliliter) was injected into each well of a 96-well microplate (Maxisorp, Nunc). Each well contained 50 microliters of the solution. The 96-well microplate was left at rest at room temperature for two hours to immobilize the virus in the wells.

PBS containing 0.05% Tween 20 was injected into each well to wash the well. The PBS had a pH of 7.4. The volume of the PBS injected into each well was 200 microliters. This was repeated twice.

PBS containing 3% skim milk (available from Wako Pure Chemical Industries, Ltd.) was injected into each well to block the hemagglutinins. The volume of the PBS injected into each well was 200 microliters. The 96-well microplate was left at rest at room temperature for one hour.

PBS containing 0.05% Tween 20 was injected into each well to wash the well. The PBS had a pH of 7.4. The volume of the PBS injected into each well was 200 microliters. This was repeated twice.

The solution A was injected into each well. The volume of the solution injected into each well was 50 microliters. The 96-well microplate was left at rest at room temperature. Thus, the VHH antibodies contained in the solution A bound to the HA protein of the virus contained in the wells.

PBS containing 0.05% Tween 20 was injected into each well to wash the well. The PBS had a pH of 7.4. The volume of the PBS injected into each well was 200 microliters. This was repeated twice.

Labelled antibodies(available from Sigma-Aldrich, trade name: Monoclonal ANTI-FLAG M2 HRP antibody produced in mouse) were diluted 10,000 fold with PBS. The thus-diluted labelled antibodies were injected into each well (50 microliters/well). Then, the 96-well microplate was left at rest for one hour in a dark place.

PBS containing 0.05% Tween 20 was injected into each well to wash the well. The PBS had a pH of 7.4. The volume of the PBS injected into each well was 200 microliters. This was repeated twice.

The color-producing agent (available from Thermo Scientific, trade name: 1-step ultra TMB-ELISA) was injected into each well (50 microliters/well). The 96-well microplate was left at rest for thirty minutes to cause the color-producing agent to react with the antibody.

A sulfuric acid aqueous solution (normal, i.e., 1 N) was injected into each well at a concentration of 50 microliters/well to cease the reaction.

The absorbance of the solution at a wavelength of 450 nanometers was measured. FIG. 4 is a graph showing the measurement result of the anti-H12N1 antibody consisting of the amino acid sequence represented by SEQ ID NO: 08.

As understood from FIG. 4, the anti-H12N1 antibody consisting of the amino acid sequence represented by SEQ ID NO: 08 has a strong bond to Hemagglutinin H12 but low cross reactivity with other hemagglutinins except for Hemagglutinin H12.

INDUSTRIAL APPLICABILITY

The present invention provides a novel antibody capable of binding to an influenza virus.

The invention claimed is:

1. An antibody that consists of an amino acid sequence, wherein said amino acid sequence consists of, in an N- to C-direction, the following structural domains:

N-FR1-CDR1-FR2-CDR2-FR3-CDR3-FR4-C wherein

FR denotes a framework region amino acid sequence and CDR denotes a complementary determining region amino acid sequence;

the CDR1 consists of an amino acid sequence represented by SYYMS (SEQ ID NO: 01)

the CDR2 consists of an amino acid sequence represented by TINTGGGSTYYADSVKG (SEQ ID NO: 02);

the CDR3 consists of an amino acid sequence represented by DGPYGGYDY (SEQ ID NO: 03); and the antibody is capable of binding to H12N1 influenza virus.

2. The antibody according to claim 1, wherein the FR1 consists of an amino acid sequence represented by EVQLVESGGGLVQPGGSLRVSCAASGFTFS (SEQ ID NO: 04);

the FR2 consists of an amino acid sequence represented by WVRQAPGKGLEWVS (SEQ ID NO: 05); and the FR3 consists of an amino acid sequence represented by RFTISRDNAKNTLYLQMDSLKSEDTAVYYCAK (SEQ ID NO: 06); and the FR4 consists of an amino acid sequence represented by WGQGTQVTVSP (SEQ ID NO: 07).

* * * * *